US010595898B2

(12) United States Patent
Krimsky et al.

(10) Patent No.: US 10,595,898 B2
(45) Date of Patent: Mar. 24, 2020

(54) DEVICE FOR MEDICAL PROCEDURE LOCALIZATION AND/OR INSERTION

(71) Applicants: William Sanford Krimsky, Forest Hill, MD (US); Curt Steven Kothera, Crofton, MD (US); Amit Navin Shah, Bethesda, MD (US); Gregory John Hiemenz, Silver Spring, MD (US)

(72) Inventors: William Sanford Krimsky, Forest Hill, MD (US); Curt Steven Kothera, Crofton, MD (US); Amit Navin Shah, Bethesda, MD (US); Gregory John Hiemenz, Silver Spring, MD (US)

(73) Assignee: InnoVital, LLC, Calverton, MD (US)

( * ) Notice: Subject to any disclaimer, the term of this patent is extended or adjusted under 35 U.S.C. 154(b) by 324 days.

(21) Appl. No.: 15/545,797

(22) PCT Filed: Jan. 21, 2016

(86) PCT No.: PCT/US2016/014250
§ 371 (c)(1),
(2) Date: Jul. 24, 2017

(87) PCT Pub. No.: WO2016/118706
PCT Pub. Date: Jul. 28, 2016

(65) Prior Publication Data
US 2018/0008305 A1    Jan. 11, 2018

Related U.S. Application Data

(60) Provisional application No. 62/106,403, filed on Jan. 22, 2015.

(51) Int. Cl.
*A61B 17/34* (2006.01)
*A61M 16/04* (2006.01)
*A61M 27/00* (2006.01)

(52) U.S. Cl.
CPC ..... *A61B 17/3403* (2013.01); *A61M 16/0488* (2013.01); *A61M 27/002* (2013.01)

(58) Field of Classification Search
CPC ............ A61B 17/3403; A61M 27/002; A61M 16/0488
See application file for complete search history.

(56) References Cited

U.S. PATENT DOCUMENTS 3,791,386 A  *  2/1974  McDonald  ........ A61M 16/0472
                                                  128/207.29
5,375,588 A     12/1994  Yoon
(Continued)

FOREIGN PATENT DOCUMENTS

WO    WO/2014/044921    3/2014
WO    WO2015050788      4/2015

OTHER PUBLICATIONS

Eastridge, Brian et al., Death on the Battlefield (2001-2011): Implications for the Future of Combat Casualty Care, Journal of Trauma and Acute Care Surgery, vol. 73, Issue 6, pp. S431-S437 (Dec. 2012).

(Continued)

*Primary Examiner* — Amber R Stiles
(74) *Attorney, Agent, or Firm* — Royal W. Craig; Gordon Feinblatt LLC

(57) ABSTRACT

A device (100) for medical procedure localization and/or insertion that can be dimensionally adjusted for different patient sizes and properly aligned and stabilized using anatomical landmarks. The device (100) for medical procedure localization and/or insertion provides an adjustable template that indexes the site of interest at the intersection of a first axis or plane and a second axis or plane. An embodiment is disclosed in which a first axis is the axillary line through the patient's axilla (armpit) and iliac crest (pelvis), and a second axis is the patient's ideal horizontal nipple line.

(Continued)

The intersection of the first and second axes is the 4th or 5th intercostal space, into which a needle and/or chest tube may be placed for decompression.

36 Claims, 8 Drawing Sheets

(56) References Cited

U.S. PATENT DOCUMENTS

| | | | |
|---|---|---|---|
| 7,824,417 | B2 | 11/2010 | Magnusson |
| 2006/0229641 | A1 | 10/2006 | Gupta |
| 2014/0058409 | A1* | 2/2014 | Bratlie .................. A61B 17/30 606/131 |
| 2014/0276418 | A1 | 9/2014 | Nelson |

OTHER PUBLICATIONS

Barton ED et al., Prehospital Needle Aspiration and Tube Thoracostomy in Trauma Victims: A Six-Year Experience With Aeromedical Crews, Journal of Emergency Medicine (1995).

Ball C. et al., "Thoracic Needle Decompression for Tension Pneumothorax: Clinical Correlation With Catheter Length" Canadian Journal of Surgery, 53:184-188(2010).

Davis DP et al., The Safety and Efficacy of Prehospital Needle and Tube Thoracostomy by Aeromedical Personnel, Prehospital Emergency Care, 9:191-197 (2005).

Netto FA et al., "Are needle decompressions for tension pneumothraces being performed appropriately for appropriate indications?", American Journal of Emergency Medicine 26:597-602 (2008).

Aylwin, C.J., 2008, "Pre-Hospital and In-Hospital Thoracostomy: Indications and Complications", Annals of the Royal College of Surgeons of England, 90(1): 54-57.

Ivey, K.M., et al., 2012, "Thoracic injuries in US combat casualties: a 10-year review of Operation Enduring Freedom and Iraqi Freedom", Journal of Trauma Acute Care Surgery, 73(6 Suppl 5): S514-S519.

Moorthy, K., Munz, Y., Dosis, A., Bann, S., Darzi, A., "The Effect of Stress-Inducing Conditions on the Performance of a Laparoscopic Task", Surgical Endoscopy, 17(9): 1481-1484 (2003).

\* cited by examiner

DEVICE FOR MEDICAL PROCEDURE LOCALIZATION AND/OR INSERTION

CROSS-REFERENCE TO RELATED APPLICATION(S)

The present application derives priority from U.S. provisional application Ser. No. 62/106,403 filed 22 Jan. 2015, and is a continuation-in-part of PC application no. PCT/US14/57717 filed 26 Sep. 2014.

BACKGROUND OF THE INVENTION

1. Field of the Invention

The present invention generally relates to medical devices for performing medical procedures, such as chest decompression and/or drainage, thoracentesis, thoracostomy, or the like and, more particularly, to an assist device using anatomical landmarks to pinpoint the procedure site. In one embodiment, a chest decompression assist device is disclosed for the drainage of air and/or fluid from the chest. Other such medical procedures for which the invention may be applied include tracheostomy, lumbar puncture, intraosseous vascular access, and arthrocentesis.

2. Description of Prior Art

Studies suggest that many wartime casualties could be avoided if interim tools and procedures could be implemented to allow non-experts to perform certain procedures before the injured patient can be transported to a higher level of care facility. For example, tension pneumothorax (collapsed lung) is among the top three most common causes of preventable combat death. Eastridge, Brian et al., "*Death on the Battlefield* (2001-2011): *Implications For The Future Of Combat Casualty Care*, Journal of Trauma and Acute Care Surgery, Volume 73, Issue 6, pp S431-S437 (December 2012). This is because the remedial procedure is often performed incorrectly.

That procedure is a needle decompression effected by insertion of an intercostal catheter (ICC) (also known as needle thoracostomy). Needle decompression involves instrument (needle) placement, and subsequent catheter placement over the needle, into the affected side of the chest, typically at the second intercostal space in the mid-clavicular line, just above the rib to avoid the intercostal artery (alternatively, the fourth or fifth intercostal space at the anterior axillary line is now an accepted site). Chest tube decompression (also known as "tube thoracostomy") involves placement of a tube through the chest wall into the pleural cavity primarily to drain an air or fluid collection from the pleural space.

It has been reported that failures occur in 30-50% of cases. Barton E D et al., *Prehospital Needle Aspiration And Tube Thoracostomy In Trauma Victims: A Six-Year Experience With Aeromedical Crews*, Journal of Emergency Medicine (1995); Ball C. et al., "*Thoracic Needle Decompression For Tension Pneumothorax: Clinical Correlation With Catheter Length*" Canadian Journal of Surgery, 53:184-188 (2010); Davis D P et al., *The Safety And Efficacy Of Prehospital Needle And Tube Thoracostomy By Aeromedical Personnel*, Prehospital Emergency Care, 9:191-197 (2005). Major reasons for failure include incorrect needle and/or chest tube location. Netto F A et al., "*Are needle decompressions for tension pneumothraces being performed appropriately for appropriate indications?*", American Journal of Emergency Medicine 26:597-602 (2008). Aylwin, C. J., 2008, "*Pre-Hospital and In-Hospital Thoracostomy: Indications and Complications*", Annals of the Royal College of Surgeons of England, 90 (1): 54-57.

There are prior art chest decompression devices/kits available, but they rely on the user to identify surface anatomical landmarks, and to use these landmarks to insert the needle/catheter. Hence, they do not address the problems of properly identifying, stabilizing and accessing the procedure site.

The foregoing problem is exacerbated on the battlefield because the procedure may need to be performed by combat medics or fellow soldiers under duress. Thoracic injuries occurred in nearly 10% of wounded personnel in recent military engagements. Ivey, K. M., et al., 2012, "*Thoracic injuries in US combat casualties: a 10-year review of Operation Enduring Freedom and Iraqi Freedom*", Journal of Trauma Acute Care Surgery, 73(6 Suppl 5): S514-S519. Tension pneumothorax, a consequence of thoracic trauma, is among the top three most common causes of preventable combat death. Eastridge, Brian et al., "*Death on the Battlefield* (2001-2011): *Implications For The Future Of Combat Casualty Care*, Journal of Trauma and Acute Cars Surgery, Volume 73, Issue 6, pp S431-S437 (December 2012). Battlefield factors include limited training and experience of combat medics relative to physicians, and the battlefield environment itself. It has been shown, for example, that stressful conditions can adversely affect clinical skill. Moorthy, K., Munz, Y., Dosis, A., Bann, S., Darzi, A., "*The Effect Of Stress-Inducing Conditions On The Performance Of A Laparoscopic Task*", Surgical Endoscopy, 17(9); 1481-1484 (2003).

A simplified and more reliable procedure is imperative. Several kits have been developed in an attempt to simplify the procedures or reduce the number of tools needed, but none have demonstrated statistically significant improvement in terms of factors such as time to completion, accuracy in placing catheter, and complication rates. This is because the developed kits still rely on the user to find and use the proper anatomical landmarks during insertion.

What is needed is an assist device for guiding medical procedures, including chest decompression, tube thoracostomies, and other percutaneous procedures, such as tracheostomy, lumbar puncture, intraosseous vascular access, and arthrocentesis, with universal applicability that significantly improves the success rate and effectiveness of performing the procedures.

SUMMARY OF THE INVENTION

In accordance with the foregoing objects, it is an object of the present invention to provide a device for medical procedure localization and/or insertion that is easy-to-use, designed with simplifying features to avoid both common and devastating errors (or at least features that significantly reduce the chance of such errors to occur), and that is effective and broadly applicable.

It is another object so provide an adjustable device for medical procedure localization and/or insertion that uses physical reference points of the anatomy (i.e., anatomical landmarks) for alignment, stabilization, instrument placement (i.e., needle or tube), instrument securement, and device anchoring. In this context it is generally understood that stabilization implies holding a component or instrument in place in a temporary manner (e.g., while unpackaging a needle), securement implies a more permanent fixing between an instrument and a component or device (e.g., a needle to a brace), anchoring implies a more permanent fixing between a component or device and a patient (e.g., a brace to a human torso) or to another device, and locking implies fixing a member of a device such that it cannot move relative to the device.

It is another object to provide a device for medical procedure localization and/or insertion that may be used by both skilled and unskilled personnel.

In accordance with the foregoing and other objects, the present invention is a device for medical procedure localization and/or insertion that can be dimensionally adjusted for different patient sizes and properly aligned, stabilized, and/or anchored using anatomical landmarks. The device for medical procedure localization and/or insertion provides an adjustable template that enables accurate identification of the proper landmarks to improve efficacy of the procedures, and to make incorrect performance difficult.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

Figure 1:
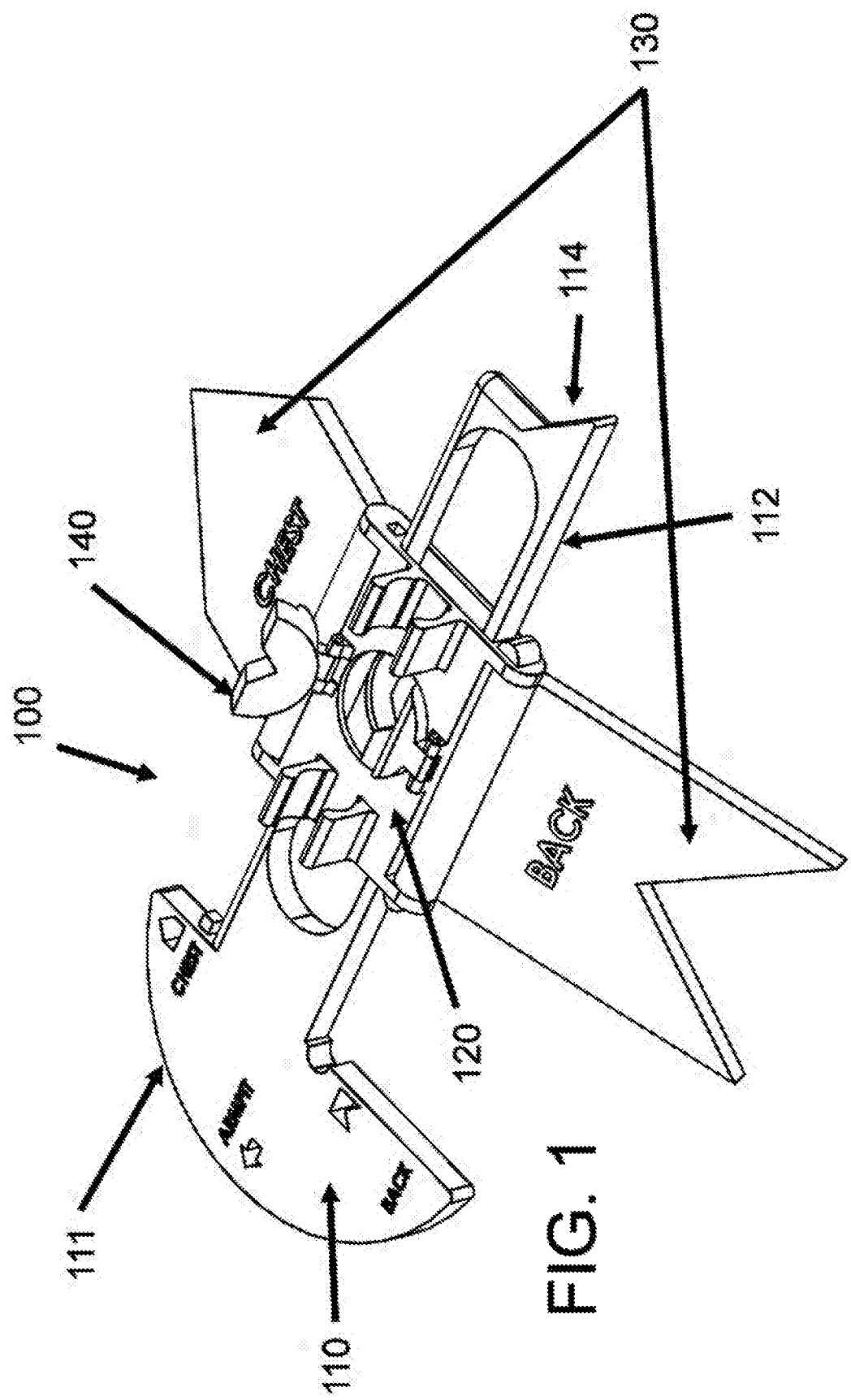
FIG. 1 is a top perspective illustration of a preferred embodiment of the device 100 for medical procedure localization and/or insertion shown for a procedure on the patient's right side (e.g., needle or chest decompression).

The present invention is a procedural assist device that improves the safety and effectiveness of certain medical procedures using anatomical landmarks to pinpoint the procedure site. The medical procedure may comprise any "site-specific procedure" herein defined as any procedure involving either localization and insertion or both, wherein at least one site of interest is identified through the intersection of two or more axes or planes, at least one of said axes or planes being determined from one or more human anatomical landmarks. The present device provides an intuitive template that reliably identifies the site of interest. Examples of such procedure include needle/chest decompression, cricothyrotomy, tracheostomy, tracheotomy, lumbar puncture, intraosseous vascular access, and arthrocentesis.

The first embodiment of the invention is herein described in the context of a device suited for chest decompression, wherein the site of interest is the 4th or 5th intercostal space along the anterior axillary line and the medical instrument of the procedure is a needle/catheter, where the catheter generally fits tightly over the needle, effectively as a single instrument. Then during the procedure, the needle is used to pierce the tissue and enter the pleural space first, after which it is removed, leaving the catheter in place.

In this context the device provides an insertion template that indexes the site of interest at the intersection of a first axis and a second axis. The first axis is the axillary line through the patient's axilla (armpit) and iliac crest (pelvis). The second axis is the patient's horizontal nipple line, a horizontal line passing through the ideal location of the nipples and generally perpendicular to the axillary line (first axis). The intersection of the first and second axes is the $4^{th}$ or $5^{th}$ intercostal space, into which the instrument (needle/catheter) is to be placed to properly accomplish the procedure (decompression). The device also secures the instrument (catheter) once inserted to avoid dislodgement and the device can be anchored to the patient.

One skilled in the art should understand that other medical procedures, such as those listed above, may involve a different first axis or plane, and/or a different second axis or plane. However, in all such cases the device provides an insertion template that indexes the intersection of a first axis or plane and a second axis or plane, wherein at least one of the first and second axes or planes are determined from one or more human anatomical landmarks. One skilled in the art will also understand that additional axes may also be employed within the same invention, such as an insertion depth hard-stop.

In addition, to enable universal application to differently sized adults, the present invention features an indexed sliding component for appropriate adjustment. The procedural assist device is easy to use by both skilled and unskilled personnel, highly effective, and has broad applicability.

As seen in FIGS. 1-4, a preferred embodiment of the device 100 for medical procedure localization and/or insertion in reference to chest decompression comprises a base component 110, a length adjustment component 120, flanges 130, and instrument securers 140. Base component 110 includes an axilla locator 111 at one end and an ilium pointer 114 at the other, and thereby references the axillary line through the patient's axilla and iliac crest. Movement of length adjustment component 120 relative to base component 110 provides the next anatomical reference with assistance from flanges 130, which are configured with added functionality as a pointer for device alignment.

A procedure for placement of device 100 for chest needle localization and/or insertion comprises the following steps (demonstrated with respect to FIG. 1);

1. Place axilla locator 111 of base component 110 in patient's axilla (armpit).

2. Position ilium pointer 114 of base component 110 toward the lateral peak of the iliac crest (pelvis), such that said pointer is directed to the highest point of the iliac crest.

3. Slide length adjustment component 120 until flanges 130 align with nipple line.

To implement the foregoing, and as seen in FIG. 1, axilla locator 111 of base 110 is defined by a superior arch segment configured, for example, as a substantially circular segment bounded by an outwardly facing arch or other convex edge to reference and identify the anatomical shape of the axilla of the patient. Base 110 extends lengthwise from axilla locator 111 in the inferior direction along extension 112 to ilium pointer 114 at the other end. The inferior extension 112 of base 110 contains an internal slot 113 to accommodate different patient sizes. Ilium pointer 114 preferably comprises a protruding indicator, such as an arrow shape. During use, ilium pointer 114 is pointed toward the lateral peak of the patient's iliac crest (i.e., pelvis), serving as a second anatomical reference point to ensure proper alignment of device 100 (i.e., defining the first axis—an axillary line).

To provide the user with information on correct orientation of device 100 relative to the patient, base component 110 preferably comprises descriptive annotations 115 including "chest", "armpit" and "back". Further, base 110 may feature geometrical shapes 116 that provide guidance to the user on correct device orientation, which may also align with other device components, such as flanges 130, when assembled correctly. Safeguards to prevent incorrect assembly may also be included, such as asymmetrical rails 118 (rounded bead on one edge 118a (FIG. 3) versus orthogonal bead on the opposite edge 118b) on the edges of inferior extension 112 of base 110 that will only fit with length adjustment component 120 in the correct orientation. Alternate geometric shapes and male-female mating characteristics 117 may be employed for the purposes of correct assembly and component orientation as well, providing additional physical and/or visual guidance to the user.

Figure 2:
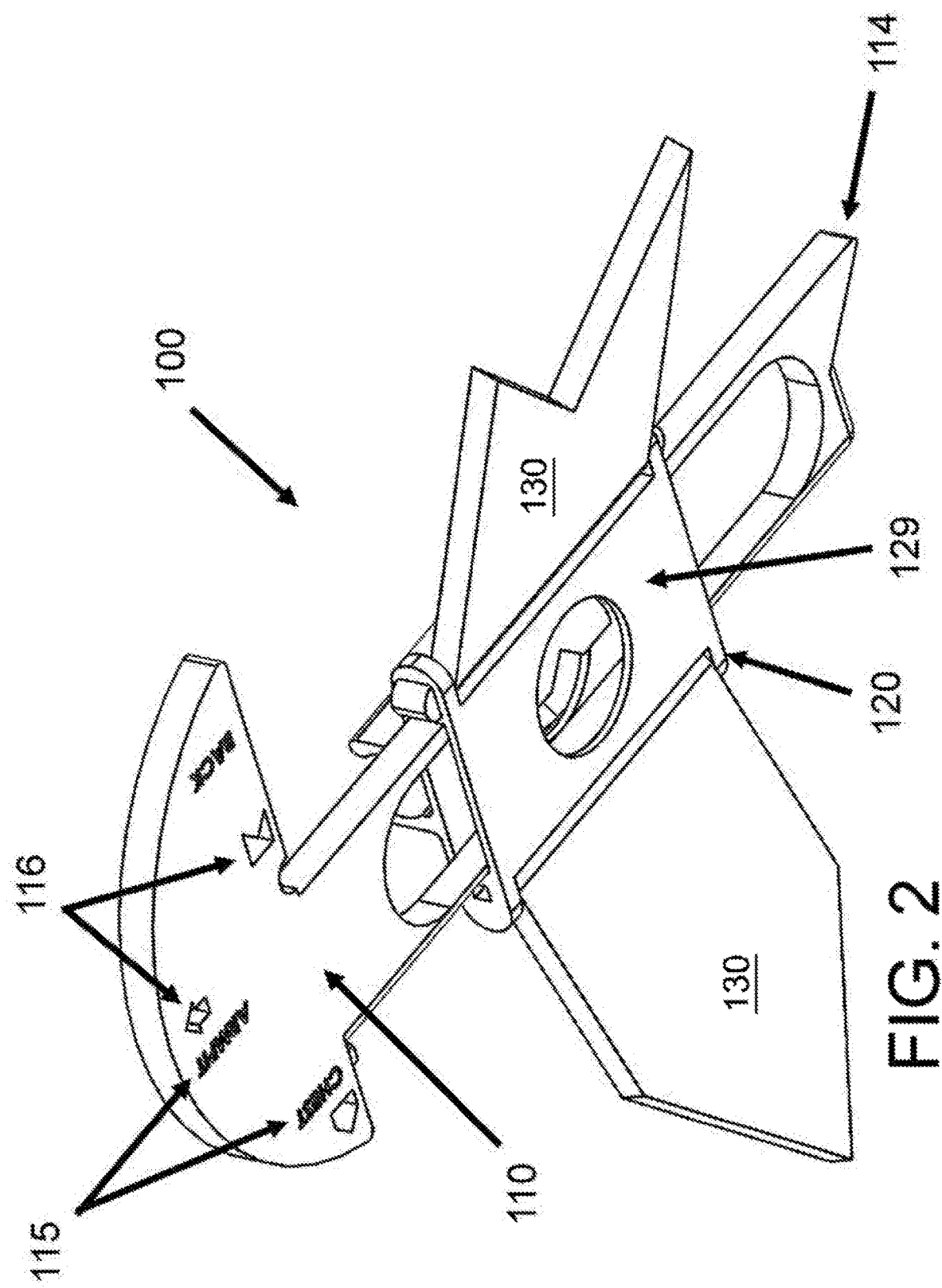
FIG. 2 is a bottom perspective illustration of the device 100 of FIG. 1.

Note in FIG. 2 that annotations 115 of base component 110 preferably appear on both lateral faces of base 110 because it must be applicable (annotations visible to user) to both the left and right side of the patient for the exemplary procedure of lateral chest decompression, though this is not necessary for all procedures. Geometric shapes 116 are also preferably visible to the user on both sides of base 110, and may extend through the thickness of base 110 for this purpose.

Figure 3:
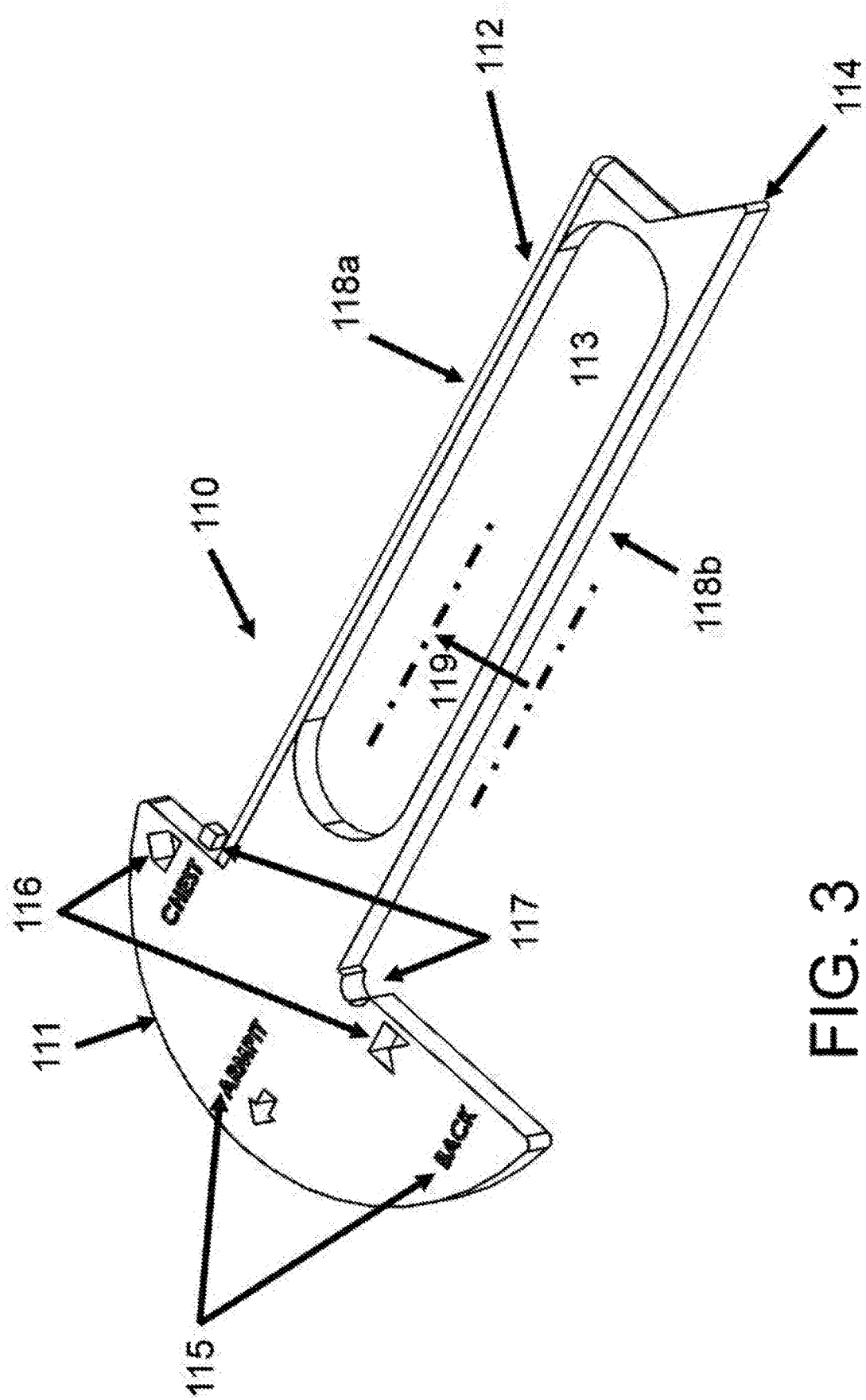
FIG. 3 is a top perspective view of the base component 110 of the device 100 of FIG. 1.

For the anatomical referencing of base component 110 shown in FIG. 3, the inferiorly extending rails 118 may be offset/biased anteriorly 119 (i.e., toward the chest) since this embodiment of device 100 is intended for chest decompression through the $4^{th}$ or $5^{th}$ intercostal space along the anterior axillary line. Hence, the asymmetrical shape of base component 110 about the coronal plane. For other such percutaneous procedures, however, this bias 119 may not be necessary and different anatomical landmarks may be referenced, with the same type of device.

With base component 110 positioned to provide anatomical references for the first axis or plane (axillary line) through the patient's axilla and iliac crest, and being anterior to that line, movement of length adjustment component 120 provides the next anatomical reference with assistance from flanges 130 to index the second axis or plane (nipple line). Flanges 130 are preferably shaped to resemble a pointer, such as an arrow, wherein the anterior flange ends in a point (e.g., tip of arrow) and the posterior flange does not (e.g., end of arrow). This is an easily identifiable visual cue for the user. Recall that base component 110 may contain geometric annotations 116 that coincide with the shapes of flanges 130 when properly oriented. The pointer defined by flanges 130 is moved by the user via length adjustment component 120 until said pointer is aligned with the patient's horizontal nipple line, thereby defining the second axis, as this defines the $4^{th}$ or $5^{th}$ intercostal space, into which the needle/catheter is to be placed to accomplish decompression. The "horizontal nipple line" is herein defined as a horizontal line passing through the ideal location of the nipples. This ideal location allows for an appropriate adjustment for those patients whose nipples are lower or higher (e.g., when they are lying on their back) than they would otherwise be found.

Figure 4:
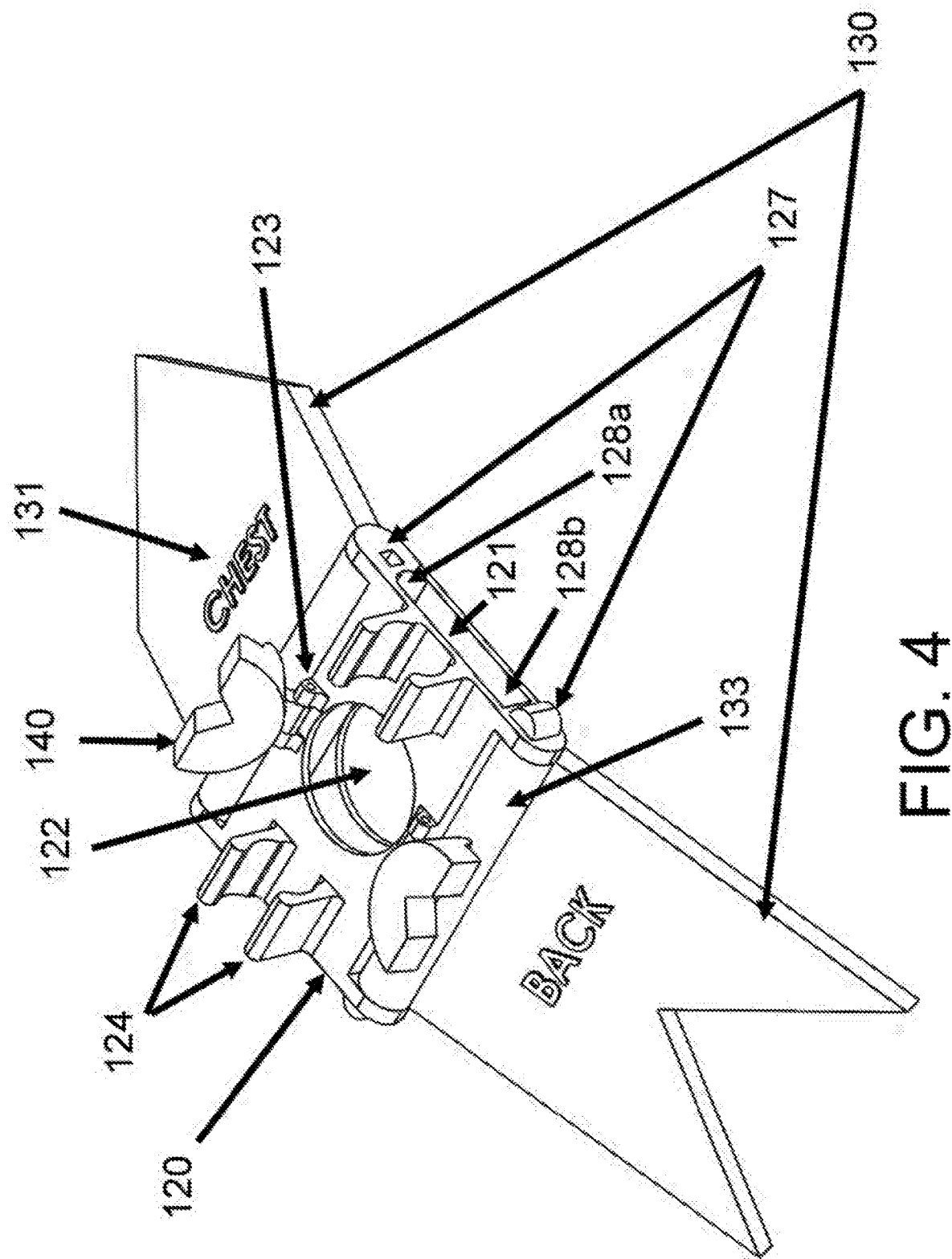
FIG. 4 is a top perspective view of the device 100 of FIG. 1 without the base component 110.

Device 100 is pictured without base component 110 in FIG. 4. Length adjustment component 120 is defined by an internal channel 121 that fits, preferably slidably, over inferior extension 112 of base component 110. As such, the anterior and posterior edges 128 of this channel 121 preferably feature geometric asymmetry, shown here as a rounded face 128a and a flat face 128b, to prevent incorrect assembly over the correspondingly asymmetric faces 118a and 118b of base extension 112. Offering more, and redundant, information to the user, length adjustment component 120 may also have different geometrically shaped features and male-female characteristics 127 to further distinguish the anterior from posterior, which mate with related base components 117. These features, along with the anterior bias, give length adjustment component 120 asymmetry about the component's coronal plane.

Contrary to base component 110 having the same global orientation relative to the patient (e.g., arch 111 being superior and slot 113 being anterior), length adjustment component 120 has a relatively flat torso side 129 (underside of FIG. 2) that is placed against the patient's body, regardless of device 100 being on the left or right side, and a non-flat side (pictured in FIG. 4) that contains other design features and is not intended to contact the patient's torso. Hence, the inclusion of and utility of the noted asymmetric design features which ensure this component orientation. This gives length adjustment component 120 asymmetry about the sagittal plane. Note also that torso side 129 of length adjustment component 120 may serve as an antiseptic applicator is some instances.

Length adjustment component 120 does preferably have symmetry about its transverse plane because it must be able to point out the correct insertion site on both sides of the patient via flanges 130.

Length adjustment component 120 is further defined by a center opening 122 (procedure area), preferably large enough to fit a human finger to allow for palpation to confirm that the proper site has been identified prior to inserting the needle/catheter (instrument). This opening 122 slides along slot 113 of base component 110 when being adjusted for the patient size.

The outer surface of length adjustment component 120 may be fitted with hinge arms 123 which allow connection to instrument securers 140. The connection is preferably articulating and most preferably pivotable. Securers 140 can be pivoted into opening 122 in a compact stowed state of device 100 and pivoted out to expose opening 122 when aligning device 100 for the procedure. Once device 100 is properly positioned, securers 140 can be pivoted back into opening 122, where they may also serve the function of providing guidance (e.g., a stop-limit) on proper needle/catheter insertion depth, in addition to securing the proximal end of the catheter in position once the distal end has been appropriately inserted and the internal needle removed. While FIG. 4 shows the insertion guide as two substantially semi-circular shaped pieces 140, the device could use a single piece that pivots into and out from the opening as required for the procedure without changing the invention. Likewise, the pivoting motion and connection described is not meant to be limiting to the invention, as other connections could be used with the same intention(s) and function(s), such as folding, sliding, and twisting securers 140 into and out of position.

The outer surface of length adjustment component 120 may also be fitted with one or two pair of opposing tabs 124, each pair forming a resilient yoke. Tabs 124 may be configured to hold the instrument (e.g., needle/catheter) in its case securely with device 100 until the user needs to perform the procedure on a patient. As shown in FIG. 4, tabs 124 are preferably resilient extensions that allow the instrument case to snap into and out of place easily.

The anterior and posterior sides of length adjustment component 120 also preferably have hinges 133 that allow pivoting connection of flanges 130. Flanges 130 rotate about hinges 133 to adjust for the size of the patient's torso, and can be used for device stabilization when aligning device 100 on the patient and when performing the procedure. Preferably, flanges 130 are a resilient material (e.g., pliable fabric straps, flexible plastic, etc.) that allows for a more compact stowed configuration of device 100, as well as allowing them to conform to the shape of the patient's body. Further, the body-side of the flanges 130 preferably has adhesive backing with easy peel-off coverings, such that flanges 130 can anchor device 100, or at least length adjustment component 120, to the patient.

The outer surface of flanges 130 may also contain annotations 131, redundant or otherwise, that provide useful information to the user. FIG. 4 shows body orientation labels 131, but instructions for use or images could also be used without changing the invention. Note also that folding or other similar types of connections can be used for flanges 130 without changing the invention. Likewise without departing from the same invention, flanges 130 and adjustment component 120 may be formed as a single unitary component (e.g., a single injection molded part) without distinct rotary hinge lines 133, provided that flanges 130 in this particular embodiment are sufficiently resilient (e.g., living hinges) for the intended purposes of the components as described.

After placement of device 100 using the method described above, the user will remove the instrument (e.g., decompression needle/catheter) from tabs 124, and open instrument securers 140. The user will palpate within opening 122 to confirm that an intercostal space is within the identified procedure site. The user will then insert the decompression needle/catheter assembly (instrument) above the located rib within opening 122 to release air or fluid from the patient's pleural space. Next, the needle is removed and the remaining catheter is secured relative to device 100, or at least length adjustment component 120, with instrument securers 140. Device 100 may be anchored by its flanges 130 relative to the patient's torso with adhesive backing (under-surface, or body-side, of arrows preferably has peel adhesive). Similarly, length adjustment component 120 may also contain a locking mechanism to fix its position relative to base 110. Said locking mechanism may include any variety of types, such as thumb screws, friction locks, cam locks, spring-loaded locks, etc.

Recall that securers 140 may also be used to provide guidance during instrument insertion by constraining the instrument in at least one direction (e.g., insertion depth hard-stop), in which securers 140 would be positioned in opening 122 after user palpation and prior to instrument insertion. In this particular case, instrument securers 140 provide a third plane (or axis) to assist the procedure.

Figure 5:
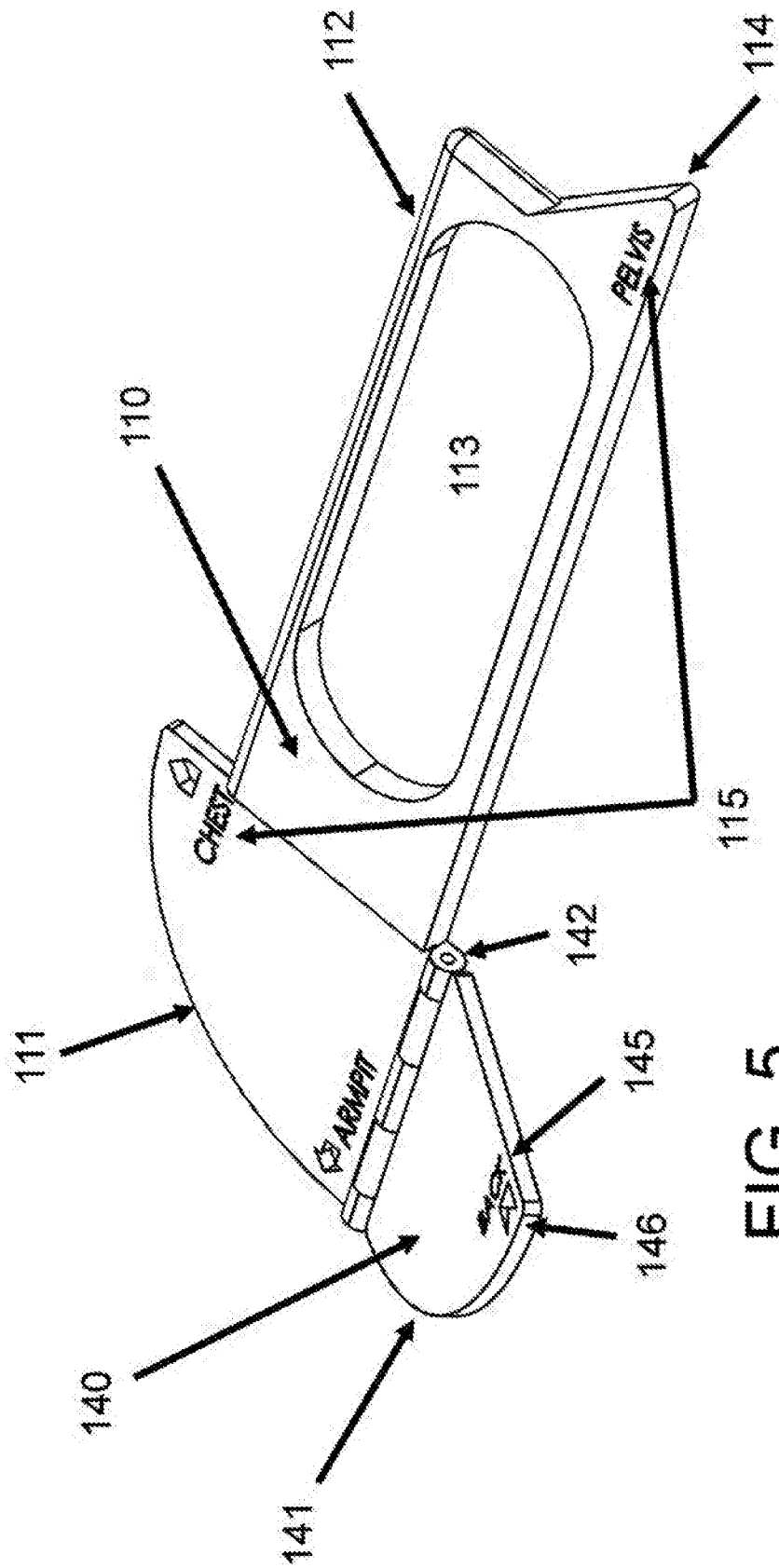
FIG. 5 is a top perspective view of an alternate embodiment of base component 110 of FIG. 1.

Keeping with the exemplary medical procedure of chest decompression, FIG. 5 shows an alternate embodiment of base component 110 wherein the unitary axilla locator 111 from FIGS. 1-3 is separated into two parts: a first part that resides with the remainder of base 110, including a segment of axilla locator 111 arch, inferior extension 112, slot 113, and pointer 114, and a second part 140 that allows more compact stowage of device 100. Here, second part 140 attaches to the primary base component 110 along hinge line 142, and when opened, axilla locator arch 111 is complemented with a similar arch 141 on second component 140.

Component 140 may also feature annotations 145 and markings 146 to help guide the user with proper orientation and use of device 100. Note that while the illustrated hinge connection 142 between primary base 110 and second component 140 is shown as a pinned hinge, other foldable or collapsible alternatives are possible without changing the invention. For example, base 110 could still be a single part with a living hinge such that section 140 can fold over the primary base section 110 to reduce stowing volume. It should also be noted in such an embodiment that the thickness of the axilla locator section 111 and folding (or hinged, etc.) sections 140 are preferably reduced from that of inferior extension 112, as is pictured in FIG. 5.

Figure 6:
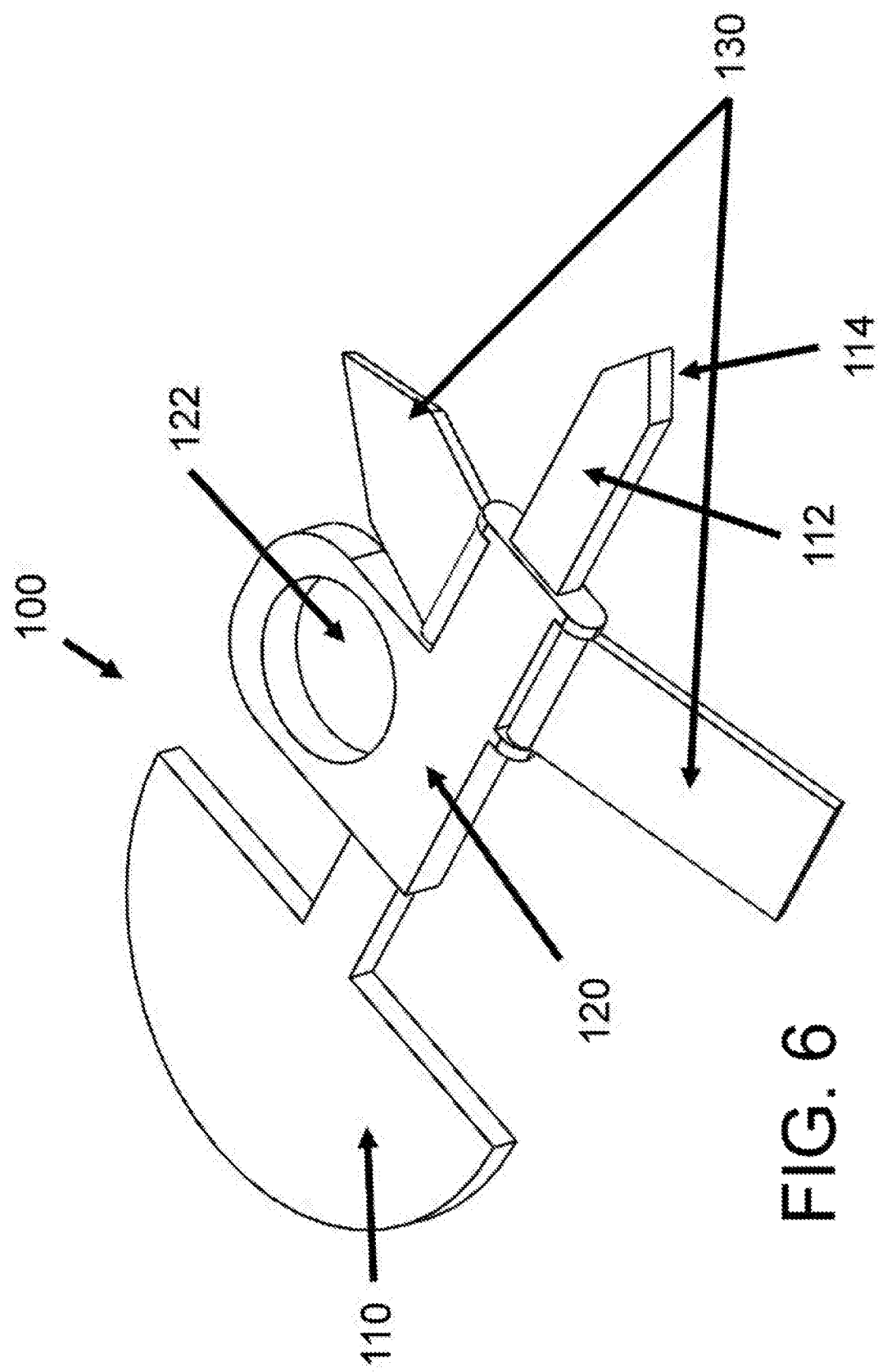
FIG. 6 is a top perspective view of an alternate embodiment of device 100 for medical procedure localization and/or insertion shown for a procedure on the patient's right side (e.g., needle or chest decompression).

Yet another alternate embodiment of device 100 for the exemplary procedure of chest decompression is shown in FIG. 6. Key differences here are that the asymmetric bias 119 of inferior extension 112 on base 110 in FIGS. 1-3 and 5 has been removed to create a substantially symmetric base 110. Slot 113 within extension 112 has been removed as well. In this embodiment (FIG. 6), the asymmetry (anterior bias) has been introduced in length adjustment component 120 by offsetting opening 122 is the preferred direction.

Figure 7:
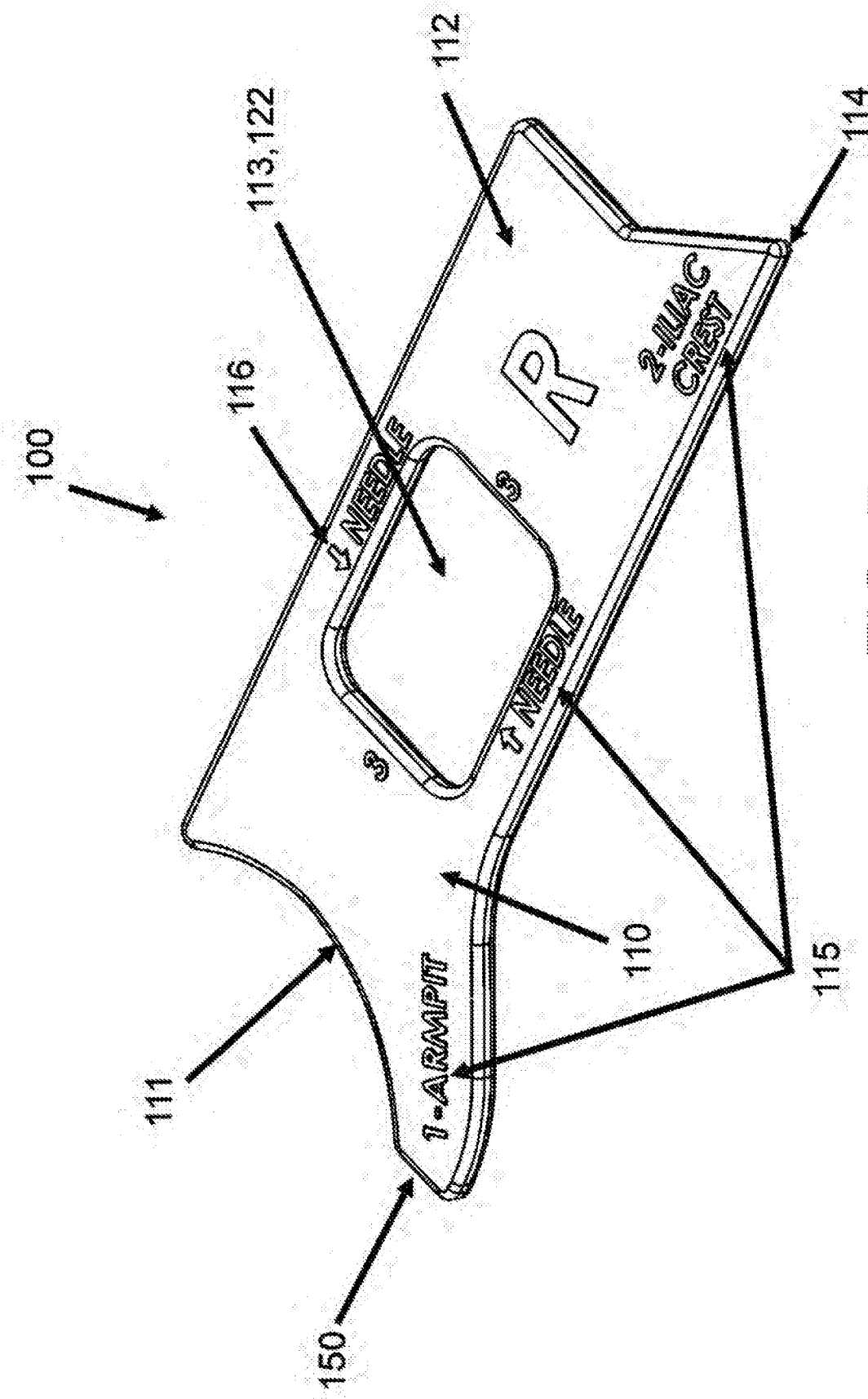
FIG. 7 is a top perspective illustration of an alternate embodiment of the device 100 for medical procedure localization and/or insertion for chest decompression.
Figure 8:
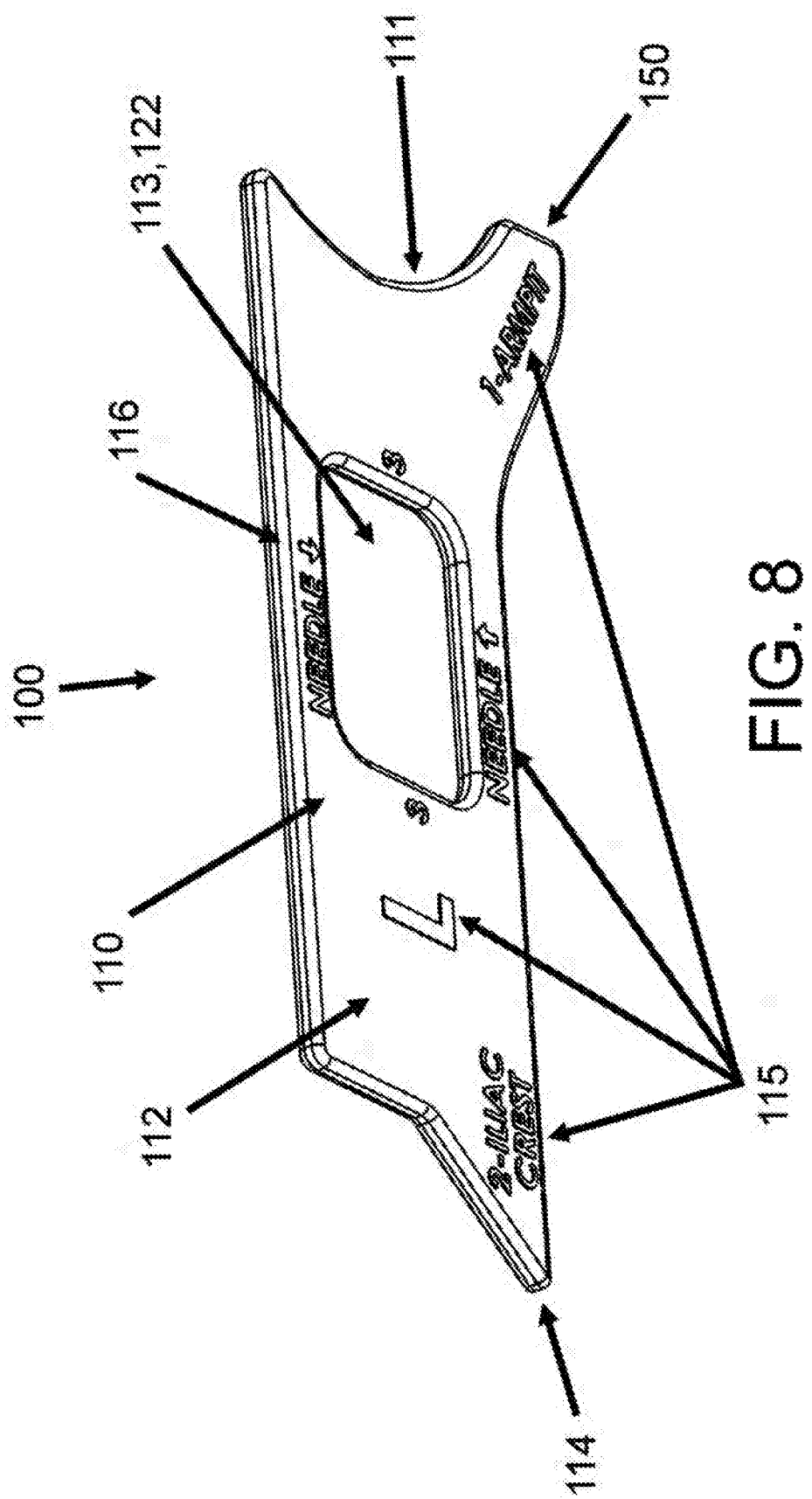
FIG. 8 is a bottom perspective view of the device 100 of FIG. 7.

Yet another alternate embodiment of device 100 for chest decompression is shown in FIGS. 7-8. This is a simplified version of the previously described embodiments containing only a base component 110. Though not pictured, this alternate embodiment may feature flanges 130 and instrument securers 140 for the same purposes as described above, though it is designed specifically not to need length adjustment component 120. As with the base components of the previous embodiments (FIGS. 1-6), this embodiment (FIGS. 7-8) is also preferably symmetric about the sagittal plane.

Base component 110 includes an axilla locator 111 at one end and an ilium locator 114 at the other end, and thereby references an axillary line through the patient's axilla and iliac crest. Opening 122 (procedure area) and internal slot 113 of the base component of FIGS. 1-3 and 5 have been merged into a single feature in this alternate embodiment of FIGS. 7-8.

A procedure for use of this single component device 100 for localization and/or insertion comprises the following steps (demonstrated with respect to FIG. 7):

1. Place axilla locator 111 of base component 110 in patient's anterior axillary fold; axillary extension 150 will be in patient's axilla (armpit).
2. Position ilium pointer 114 of base component 110 toward the lateral peak of the iliac crest (pelvis), such that said pointer is directed to the highest point of the iliac crest.
3. Palpate within opening 122 to find an intercostal space of patient.

To implement the foregoing, and as seen in FIG. 7, axilla locator 111 of base 110 is defined by a superior arch segment configured, for example, as a substantially circular segment bounded by an inwardly facing arch or other concave edge to reference and identify the anatomical shape of the anterior axillary fold of the patient. Base 110 extends lengthwise from axilla locator 111 in the inferior direction along extension 112 to ilium pointer 114 at the other end. Inferior extension 112 of base 110 contains an internal slot 113 to accommodate different patient sizes, and also acts as opening 122 that defines the procedure area. As such, slot 113/opening 122 is dimensionally designed to identify an acceptable intercostal space for a range of anatomical sizes. During use, ilium pointer 114 is pointed toward the lateral peak of the patient's iliac crest (i.e., pelvis), serving as a second anatomical reference point to ensure proper alignment of device 100 (i.e., defining the first axis—the axillary line or anterior axillary line).

To provide the user with information on correct orientation of device 100 relative to the patient, base component 110 preferably comprises descriptive annotations 115 including "armpit", "iliac crest" and "needle". Further, base 110 may feature geometrical shapes 116 that provide guidance to the user on correct device orientation and/or usage. Base 110 is also preferably asymmetric about the coronal plane to prevent incorrect usage. Preferable examples of such asymmetry are ilium pointer 114 at the inferior edge and axillary extension 150 at the superior edge.

Note in FIG. 8 that annotations 115 of base component 110 preferably appear on both lateral faces of base 110 because it must be applicable (annotations visible to user) to both the left and right side of the patient for the exemplary procedure of chest decompression, though this is not necessary for all procedures. Geometric shapes 116 are also preferably visible to the user on both sides of base 110.

With base component 110 positioned to provide anatomical references for the first axis or plane (axillary line) through the patient's axilla/anterior axillary fold and iliac crest, opening 122 indexes the next anatomical reference. Slot 113/opening 122 defining the procedure area is sized such that intercostal spaces appearing within said slot/opening are acceptable procedure locations on the patient, regardless of their size. The user simply palpates in opening 122 to identify an intercostal space and inserts the instrument to accomplish decompression. It is understood that different intercostal spaces may be identified in patients of different heights, but a range of intercostal spaces are acceptable locations (e.g., $3^{rd}$ to $5^{th}$), and anthropometric data has been used to size slot 113/opening 122 accordingly. It should also be noted that a similar single component device 100 may also be used to accomplish chest decompression through the anterior approach, where base 110 references the patient's clavicle and uses the pointer 114 to help the user identify the mid-clavicular line. In this instance, slot 113/opening 122 are sized for an acceptable range of anterior intercostal spaces (e.g., $2^{nd}$ or $3^{rd}$).

In an alternate embodiment, device 100 may be adapted to enable conversion from a more temporary medical instrument to a more durable medical instrument or medical device such as, but not limited to, conversion from a decompression catheter to a chest tube or from a cricothyrotomy tube to a tracheostomy tube. Depending on the medical procedure of interest, this conversion may be via the procedure site identified by device 100 through the first and second axes or planes, or via a second procedure site referenced from the first procedure site. For example, a decompression needle/catheter and chest tube may both be placed in the $4^{th}$ or $5^{th}$ intercostal space along the anterior axillary line, whereas a cricothyrotomy tube and tracheotomy tube are placed in different procedure sites, both of which are referenced from many of the same anatomical landmarks.

It should now be apparent that the device for assisting percutaneous procedures in the various embodiments described above will significantly improve the success rate and effectiveness of performing the relevant procedure. Device 100 mimics the expert medical approach, yet decreases the skill level necessary to perform procedure via annotations for user orientation and instruction, and geometric features for foolproof assembly and bilateral use.

The above-described device may also be used in preparation for percutaneous procedures or alternatively to train for such procedures. For example, a medic may simply wish to pre-sire each of his/her soldiers for the relevant procedure and/or use device 100 to make a mark on a patient (i.e., using a marker to outline the procedure site and then put the device aside and perform the chest decompression). Those skilled in the art will appreciate that various anatomic landmarks may be used to place drains in the chest for distinct purposes. Non-limiting examples include the mid-clavicular line for anterior chest drainage and anterior or mid-axillary lines for lateral chest drainage. Posterior chest drainage may also be accomplished with such a device through the use of surface anatomical landmarks.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

INDUSTRIAL APPLICABILITY

Studies suggest that many casualties could be avoided if interim tools and procedures could be implemented to allow non-experts to perform certain procedures before the injured patient can be transported to a higher level of care facility/provider. What is needed is an assist device for guiding performance of certain medical procedures, including chest decompression and/or drainage, thoracentesis, thoracostomy, and other percutaneous procedures or the like, in each instance using anatomical landmarks to pinpoint the procedure site. The present invention is an innovative device for performing such procedures with universal applicability that significantly improves the success rate and avoids complications when performing the procedures.

What is claimed is:
1. A device for assisting, preparing for, or training for a medical procedure, said procedure entailing localization, incision, or insertion at a procedure site on a human patient, said device comprising:
 a locator base extending from a first end to a second end, said locator base having a shape at said first end configured to index contact with a first thoracic anatomical landmark defined by a sub-epidermal structure, and said locator base having a shape at said second end configured for visual or physical alignment with a second anatomical landmark that is caudad to said first thoracic anatomical landmark, said locator base thereby indexing a first reference point at said first thoracic anatomical landmark and a second reference point at said second caudad anatomical landmark, and a first axis extending between said first reference point and said second reference point;
 a first movable member slidably attached to said locator base for movement along said first axis until alignment with a third anatomical landmark, said first movable member thereby indexing a third reference point at said third anatomical landmark, said third reference point being along a second axis that intersects said first axis; and
 a guide for indicating said procedure site at an intersection of said first axis and second axis.
2. The device of claim 1, further comprising one or more flanges.

3. The device of claim 2, wherein said one or more flanges are movable to a plurality of positions.

4. The device of claim 2, wherein said one or more flanges are pivotally attached to said first movable member.

5. The device of claim 2, wherein said one or more flanges comprise an adhesive coating.

6. The device of claim 2, wherein said one or more flanges comprise two opposing flanges to anchor and/or stabilize said device.

7. The device of claim 1, further comprising visual instructional indicia including any one or more from among the group consisting of wording, labeling, numbering, arrows, hash marks, geometrical shapes, illustrations, text instructions and indices.

8. The device of claim 1, wherein said first movable member is linearly translatable along said locator base.

9. The device of claim 8, wherein said first movable member comprises an aperture, and said locator base comprises a slot, and the aperture of said first movable member is translatable along the slot of said locator base for indexing said intersection.

10. The device of claim 1, further comprising a locking mechanism for locking said first movable member in a position.

11. The device of claim 1, wherein said guide further comprises an instrument securer for constraining an instrument in at least one degree-of-freedom for said medical procedure at said site.

12. The device of claim 1, wherein said medical procedure comprises any one from among a group consisting of chest decompression, chest drainage, cricothyrotomy, tracheostomy, tracheotomy, lumbar puncture, intraosseous vascular access, thoracentesis, or arthrocentesis.

13. The device of claim 1, wherein said device enables conversion of a temporary decompression, drainage or access instrument to another decompression, drainage or access instrument.

14. The device of claim 1, further comprising at least one instrument securer.

15. The device of claim 14, wherein said instrument securer indexes an axis or plane of said procedure.

16. The device of claim 1, wherein said locator base is configured with a hinge.

17. The device of claim 1, further comprising a second movable member movably attached to said first movable member for defining a third axis or plane to assist said medical procedure.

18. The device of claim 17, wherein said third axis or plane indicates insertion depth for a medical instrument when performing said medical procedure.

19. The device of claim 1, wherein said first thoracic anatomical landmark consists of said patient's axilla.

20. The device of claim 1, wherein said first thoracic anatomical landmark consists of said patient's clavicle.

21. The device of claim 1, wherein said second anatomical landmark that is caudad to said first thoracic anatomical landmark consists of said patient's iliac crest.

22. The device of claim 1, wherein said third anatomical landmark consists of said patient's nipple.

23. The device of claim 1, wherein said second anatomical landmark that is caudad to said first thoracic anatomical landmark consists of said patient's sternum.

24. The device of claim 1, wherein said first axis corresponds to said patient's mid-clavicular line.

25. The device of claim 1, wherein said first axis corresponds to said patient's axillary line.

26. The device of claim 1, wherein said second axis corresponds to said patient's nipple line.

27. A device for assisting percutaneous procedures on a human patient, comprising:
a base extending from a first end to a second end, said base having a first shape at said first end configured to index contact with a first thoracic anatomical landmark, said base having a second shape at said second end configured for visual or physical alignment with a second anatomical landmark that is caudad to said first thoracic anatomical landmark, said base thereby indexing a first reference point at said first thoracic anatomical landmark and a second reference point at said second caudad anatomical landmark, said first and second reference points being along and a first axis extending between said first reference point and said second reference point;
at least one adjustable component attached to said base for linear sliding movement along said first axis until alignment with a third anatomical landmark along a second axis that intersects said first axis; and
a guide that assists percutaneous access at a procedure site at an intersection of said first axis and second axis.

28. A device for assisting, preparing for, or training for a medical procedure, said procedure entailing localization, incision, or insertion at a procedure site on a human patient, said device comprising:
a locator base extending from a first end to a second end,
said locator base having a first shape at said first end configured to index contact with a thoracic anatomical landmark and thereby indexing a first point,
said locator base having a second shape at said second end configured for visual or physical indexing of an anatomical landmark that is caudad to said thoracic anatomical landmark and thereby indexing a second point,
said first and second points being along a first axis extending between said first point and said second point; and
a guide comprising an aperture through said locator base centered at an intersection of said first axis and a second axis that is offset from one of said thoracic anatomical landmark and caudad anatomical landmark and generally perpendicular to said first axis for indicating said procedure site.

29. The device of claim 28, wherein said thoracic anatomical landmark consists of said patient's axilla.

30. The device of claim 28, wherein said thoracic anatomical landmark consists of said patient's clavicle.

31. The device of claim 28, wherein said anatomical landmark that is caudad to said thoracic anatomical landmark consists of said patient's iliac crest.

32. The device of claim 28, wherein said anatomical landmark that is caudad to said thoracic anatomical landmark consists of a point on said patient's mid-clavicular line.

33. The device of claim 28, wherein said anatomical landmark that is caudad to said thoracic anatomical landmark consists of said patient's sternum.

34. The device of claim 28, wherein said first axis corresponds to said patient's mid-clavicular line.

35. The device of claim 28, wherein said first axis corresponds to said patient's axillary line.

36. A device for assisting, preparing for or training for a medical procedure, said procedure entailing localization, incision, or insertion at a procedure site on a human patient, said device comprising:

a locator base extending from a first end to a second end, said locator base having a first shape at said first end configured to index contact with a first thoracic anatomical landmark to thereby index a first point, said locator base having a second shape at said second end configured for visual or physical alignment with a second anatomical landmark that is caudad to said first thoracic anatomical landmark, said locator base thereby indexing a first reference point at said first thoracic anatomical landmark and a second reference point at said second caudad anatomical landmark, said first and second reference points being along a first axis extending between said first thoracic reference point and said second caudad reference point;

a first movable member movably attached to said locator base for linear translation along said first axis; and a guide on said movable member for indicating said procedure site relative to said first axis, relative to at least one different anatomical landmark.

* * * * *